United States Patent
Stobrawa et al.

(10) Patent No.: US 11,351,061 B2
(45) Date of Patent: *__Jun. 7, 2022__

(54) OPTICAL SYSTEM FOR A LASER THERAPY INSTRUMENT

(71) Applicant: Carl Zeiss Meditec AG, Jena (DE)

(72) Inventors: Gregor Stobrawa, Jena (DE); Mark Bischoff, Jena (DE)

(73) Assignee: Carl Zeiss Meditec AG, Jena (DE)

( * ) Notice: Subject to any disclaimer, the term of this patent is extended or adjusted under 35 U.S.C. 154(b) by 180 days.

This patent is subject to a terminal disclaimer.

(21) Appl. No.: 16/684,048

(22) Filed: Nov. 14, 2019

(65) Prior Publication Data
US 2020/0237554 A1 Jul. 30, 2020

Related U.S. Application Data

(63) Continuation of application No. 14/116,471, filed as application No. PCT/EP2012/054743 on Mar. 19, 2012, now Pat. No. 10,478,340.

(30) Foreign Application Priority Data

May 13, 2011 (DE) ...................... 10 2011 075 799.6

(51) Int. Cl.
*A61F 9/008* (2006.01)

(52) U.S. Cl.
CPC .......... *A61F 9/008* (2013.01); *A61F 9/00825* (2013.01); *A61F 9/0084* (2013.01);
(Continued)

(58) Field of Classification Search
CPC .... A61F 2009/0087; A61F 2009/00872; A61F 2009/00874; A61F 9/00825; A61F 9/0084; A61F 9/008–9/013
(Continued)

(56) References Cited

U.S. PATENT DOCUMENTS

| 5,837,962 A | 11/1998 | Overbeck |
| 6,741,359 B2 | 5/2004 | Wei |

(Continued)

FOREIGN PATENT DOCUMENTS

| DE | 10 2005 013 949 A1 | 9/2006 |
| DE | 10 2008 027 358 A1 | 12/2009 |

(Continued)

OTHER PUBLICATIONS

European Search Report for Application No. 17167182.9, dated Nov. 23, 2017, 7 pages.

(Continued)

*Primary Examiner* — Jonathan T Kuo

(74) *Attorney, Agent, or Firm* — DeWitt LLP

(57) ABSTRACT

An optical system for a laser therapy instrument for the application of laser radiation on and in the eye, includes a femtosecond laser, an objective. The objective or at least one lens or lens group of the objective is shiftable in the direction of the optical axis being intended for shifting of the focus position from the region of the cornea to the region of the crystalline lens and vice versa. The optical system may include at least two optical assemblies designed for the axial variation of the focus of the therapeutic laser radiation, with the focus variation range Δz differing between the individual assemblies and a changing device, designed for the insertion of any one of these assemblies into the therapeutic laser beam path at a time.

14 Claims, 2 Drawing Sheets

Related U.S. Application Data

(60) Provisional application No. 61/485,995, filed on May 13, 2011.

(52) U.S. Cl.
 CPC ............... *A61F 2009/0087* (2013.01); *A61F 2009/00872* (2013.01); *A61F 2009/00874* (2013.01)

(58) Field of Classification Search
 USPC ......................................................... 606/4–6
 See application file for complete search history.

(56) References Cited

U.S. PATENT DOCUMENTS

| | | | |
|---|---|---|---|
| 8,617,147 B2 | 12/2013 | Knox | |
| 9,554,943 B2 | 1/2017 | Sondermann | |
| 10,478,340 B2 * | 11/2019 | Stobrawa | A61F 9/008 |
| 2002/0060778 A1 | 5/2002 | Su | |
| 2002/0097379 A1 * | 7/2002 | Goldfain | A61B 3/156 |
| | | | 351/221 |
| 2003/0208125 A1 * | 11/2003 | Watkins | A61B 3/12 |
| | | | 600/473 |
| 2006/0187462 A1 * | 8/2006 | Srinivasan | A61B 3/102 |
| | | | 356/479 |
| 2008/0205249 A1 | 8/2008 | Bae | |
| 2009/0131921 A1 | 5/2009 | Kurtz | |
| 2009/0137993 A1 * | 5/2009 | Kurtz | A61F 9/00736 |
| | | | 606/6 |
| 2009/0299347 A1 | 12/2009 | Vogler | |
| 2011/0028953 A1 | 2/2011 | Raksi | |
| 2011/0071509 A1 | 3/2011 | Knox | |

FOREIGN PATENT DOCUMENTS

| | | |
|---|---|---|
| DE | 10 2009 005 482 A1 | 7/2010 |
| DE | 11 2008 002 511 T5 | 7/2010 |
| DE | 11 2008 002 448 T5 | 11/2010 |
| GB | 2 359 375 A | 8/2001 |
| WO | WO 2012/130480 A1 | 10/2012 |

OTHER PUBLICATIONS

Application and File History for U.S. Appl. No. 14/116,471, filed Jan. 2, 2014. Inventors: Gregor Stobrawa et al.

* cited by examiner

OPTICAL SYSTEM FOR A LASER THERAPY INSTRUMENT

CROSS-REFERENCE TO RELATED APPLICATIONS

The present application a continuation of application Ser. No. 14/116,471, filed Jan. 2, 2014, which is a National Phase entry of PCT Application No. PCT/EP2012/054743, filed Mar. 19, 2012, which claims priority from DE Application No. 10 2011 075 799.6, filed May 13, 2011, and U.S. patent application Ser. No. 61/485,995, filed May 13, 2011, which applications are incorporated by reference herein in their entirety.

TECHNICAL FIELD

The present invention relates to an optical system for a laser therapy instrument for the application of laser radiation on and in the eye, suited particularly for laser surgery of the cornea and/or of the crystalline lens.

BACKGROUND

Laser therapy instruments are used, e.g., for correcting an ametropia of the human eye by a laser-surgical operation of the cornea. For this purpose, a lid is formed on the outer surface of the cornea, which lid is attached along one edge and is therefore known as a flap, and the thickness of which is substantially smaller then the thickness of the cornea. For correction, this flap is folded back, and from the surface of the region of the cornea that is now exposed, tissue is removed thereupon by application of a laser beam pulsed in the femtosecond range, in order to change the curvature of the cornea. Such an instrument is described in DE 10 2005 013 949 A1.

By contrast, a laser system described in DE 10 2008 027 358 A1 is intended for the analysis and treatment of the crystalline lens. Here, laser radiation also pulsed in the femtosecond range is focussed on to selected target spots in the region of the crystalline lens. At this wavelength, the detection of the laser light backscattered in the crystalline lens is possible at the greatest accuracy, and a refractive-surgical therapy of the crystalline lens can be performed with high precision.

Typically, in either case the interaction between the ultra-short laser pulses and the tissue takes place in a small volume, hereafter referred to as focus volume. Situated within the focus volume is the interaction zone, in which the structural change, section or removal of the tissue takes place. The laser focus must be precisely positioned at the locus of the desired interaction. This is done with an optical focusing system, which projects the parallel laser beam from infinity at the object side into the treatment plane on the image side.

This means that the precision achievable in the therapy is determined by the precision accuracy on the one hand, but also by the size of the interaction zone on the other. The size of the interaction zone, in turn, with a given laser pulse width, is essentially defined by the size of the focus volume. The smaller the focus volume, the smaller is the interaction zone, and the lesser is the risk of damage to the surrounding tissue, because with a small focus volume, the photon density needed for the treatment effect is achieved already with a very low laser pulse energy, such as about 10 nJ to 200 nJ; as a result, the energy input to the in the vicinity of the interaction zone is low.

The size of the focus volume varies with the parameters of the optical system and with the wavelength of the therapeutic laser radiation. In other words: in connection with a given wavelength, the desired small size of the focus volume is made possible by small aberrations and a fairly high numerical aperture. With increasing numerical aperture, not only the lateral dimension of the focus shrinks, but also its axial dimension. From the viewpoint of application, the numerical aperture should preferably be as high as possible.

The possibilities known in prior art of medical treatment of the cornea lying at the periphery of the eye on the one hand, and of the crystalline lens lying within the eye on the other, have the disadvantage that the instruments available satisfy the requirements of their respective special purpose only, which means that they differ, especially with regard to the focus position in the eye, the aperture and the size of the focus volume, to such an extent that they are designed and suitably either for therapy of the cornea alone or for therapy of the crystalline lens alone.

This requires extensive instrumentation that is ineffective both with regard to purchase costs and because several separate instruments are used below their capacity most of the time. In addition, setting up the several instruments separately for examining and treating the same patient eye is time-consuming.

While laser therapy instruments that can treat both the crystalline lens and the cornea are known, they are originally optimized only for the treatment of the crystalline lens. They can be used, e.g., to make access cuts for cataract operations, but the precision achievable with them is insufficient for creating a flap. This is because axial focus movements by several millimetres are required if the laser focus is to reach the entire anterior segment of the eye including the crystalline lens.

An essential problem to be solved in that respect is the fact that all object-side movements serving to vary the focus position (varying the parameters of the therapeutic laser beam before it enters the optical focussing system, e.g., by the shifting of lenses within the optical systems arranged further up the beam or by the movement of scanning mirrors) will inevitably result in a change of beam paths within the optical focussing system. The term "optical focussing system", in this context, stands for the objective from which the therapeutic laser radiation exits and is focussed on and directed at the eye. If, e.g., the axial position of the laser focus is shifted in this way, the aberrations occurring as a function of this variation will have a disadvantageous effect on the focus volume.

An optical focussing system or an objective that is optimized only for a particular focus position in axial direction always is a compromise between the spatial region accessible by the focus position and the size of the aberrations occurring within this region. As the same is true also for the lateral extension of the spatial region accessible by the laser focus, there is always a restriction of the entire spatial region in which the necessary focus quality is to be achieved.

SUMMARY

Departing from this, the invention is based on the problem of creating an optical system for a laser therapy instrument which can be used alternately for laser surgery of the cornea and of the crystalline lens with high precision in both uses.

According to the invention, this problem is solved by an optical system having the features as described and claimed.

Note on the definition of terms: In the sense of the invention, the term "axial" defines the direction of the Z coordinate, and the term "lateral" defines the X and Y coordinate directions.

The inventive idea is based on the fact that the anterior segment of the eye consists essentially of two tissue regions that are of interest to laser surgery, i.e. the region of the cornea with a thickness of approximately 0.5 to 2 mm measured in the direction of radiation on the one hand, and the region of the crystalline lens with a substantially greater thickness of about 2 mm to 6 mm on the other hand. In between there is the anterior chamber filled with aqueous humour.

Consequently, for the most frequent therapies of the eye it is not necessary to design the optical system in such a way that the entire anterior segment of the eye can be accessed by the focus with an object-side axial scanning movement. It is sufficient to direct the focus separately to the region of the crystalline lens and the region of the cornea. Because of that, the actually very large object-side Z scanning range is limited to two separate tissue regions lying between the front surface of the cornea and the rear surface of the lens. While these tissue regions are spaced at a considerable distance from each other, one of them covers only slightly more than the cornea thickness and the other only slightly more than the thickness of the crystalline lens. This makes it possible to induce fewer aberrations.

According to an example embodiment of the invention, a configurable objective is used; in a first configuration, the focus position lies in a region comprising the cornea, and in a second configuration, the focus position lies in a region comprising the crystalline lens and the lens capsule. Both configurations can be achieved by at least one of the following measures:

Changes of air gaps between single or several lenses,
Changes of lens radii of one or several lenses,
Changes of refractive index of one or several lenses,
Insertion or exchange of single lenses or lens groups.

In that way, at least the two states are achieved that are optimally adapted to the respective focus position and thus have the least aberrations in these two configurations. This makes it possible to precisely vary the focus axially by object-side divergence variation in the region of the cornea or of the crystalline lens, respectively.

The optical assemblies arranged before the focussing objective in the direction of radiation for the purpose of divergence variation are so designed optically that the focus variation ranges Δz for the cornea and also for the crystalline lens including the lens capsule are covered completely. According to the invention this is accomplished with certain "optical gear" ratios of the moved lenses or lens groups in these assemblies, in the context of the invention also called expanders. The gear ratio is designed to be a large as possible in order to achieve a very high accuracy of the Z position of the focus. According to the invention, the optical gear ratios between lens or lens group movements and focus position changes are computed or measured, saved as system parameters and taken into account by way of correction when the focus position is varied.

Axial resolution losses occurring upon switching between the two configurations are avoided in that the optical design of the expanders is coupled to the configuration change, for example, in that two expanders in the therapeutic laser beam path are exchanged against one another. Both expanders have beam path lengths which are independent of one another and are inserted into the beam path alternatingly depending on the configuration selected by the user.

Because of the varied depths of the focus positions in the anterior segment of the eye, there is, for each focus position, a maximum useful aperture, which is limited because of the free optical diameter of the optical focussing system and because of the anatomy of the eye, especially due to the shadowing of the iris in treatments of the crystalline lens. In case of smaller axial focus positions, such as occurring in treatments of the cornea, larger apertures can be used to advantage, with the associated advantages of the more compact focus volume, whereas in case of greater axial focus positions, i.e. in the region of the crystalline lens, it is of advantage not to fully utilize the technically available aperture of the optical focussing system but rather to use only the aperture that can effectively be utilized depending on the application. According to the invention, this is done by means of a reduced beam diameter at the entrance pupil of the optical focussing system.

The adaptation of the beam diameter to the configuration selected is accomplished by changing the expanders. In this way, a combined optical system results, which is adapted optimally to treatment of the cornea on the one hand, and, likewise optimally, to treatment of the crystalline lens on the other; this means that in either case the axial resolution is as high, and the numerical aperture as large, as possible technically and with regard to the application, while the aberrations of the system are, in either case, as small as possible.

It is also within the scope of embodiments of the invention to introduce a third axial focus variation range Δz into optical system, e.g., for the purpose of manipulations in the anterior chamber of the eye, for vitreous body surgery or for therapies in the region of the retina.

The configuration change will also cause a change of field curvature depending on the real focus position. It is within the scope of the invention to compute or measure the field curvature, to save it as a system parameter as well and to take it into account in focussing by way of correction.

The above summary is not intended to describe each illustrated embodiment or every implementation of the subject matter hereof. The figures and the detailed description that follow more particularly exemplify various embodiments.

BRIEF DESCRIPTION OF THE DRAWINGS

Below, the invention will be explained in greater detail with reference to exemplary embodiments. In the accompanying drawings, a preferred embodiment.

Subject matter hereof may be more completely understood in consideration of the following detailed description of various embodiments in connection with the accompanying figures, in which.

Figure 1:
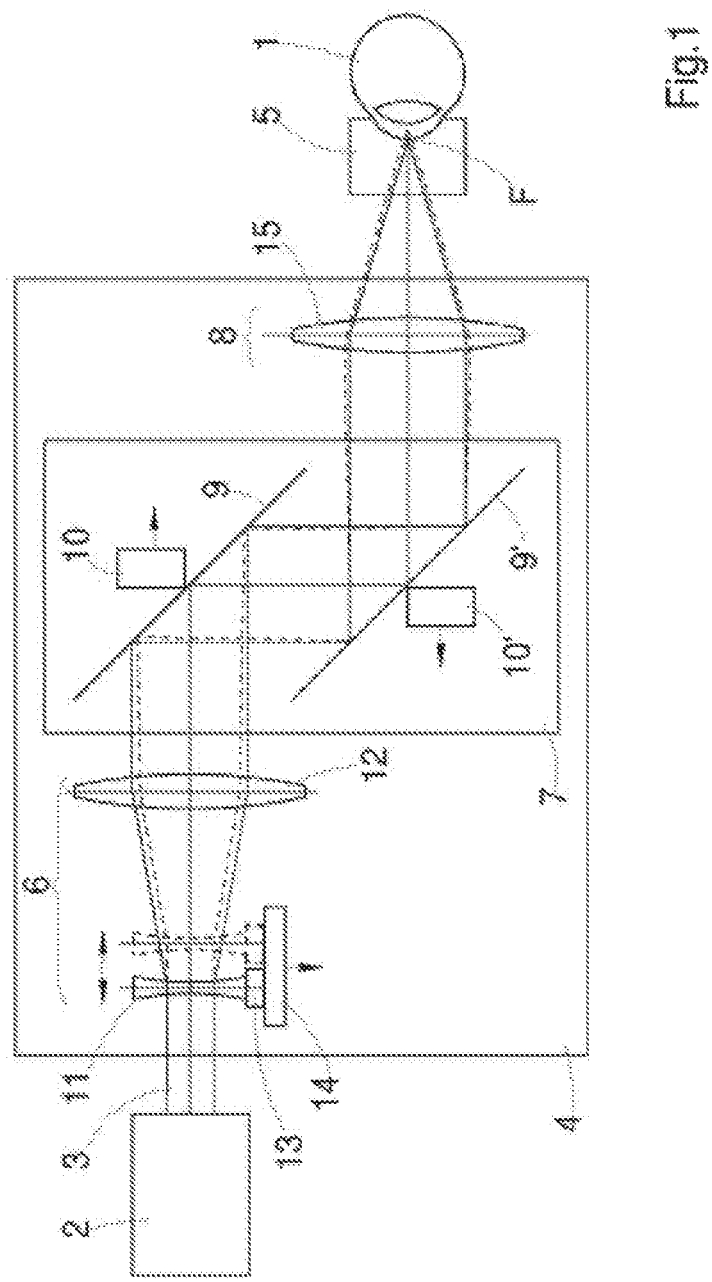
FIG. 1 is a schematic illustration of the optical system for a laser therapy instrument for the application of laser radiation as known in prior art.

While various embodiments are amenable to various modifications and alternative forms, specifics thereof have been shown by way of example in the drawings and will be described in detail. It should be understood, however, that the intention is not to limit the claimed inventions to the particular embodiments described. On the contrary, the intention is to cover all modifications, equivalents, and alternatives falling within the spirit and scope of the subject matter as defined by the claims.

DETAILED DESCRIPTION OF THE DRAWINGS

The optical system shown in FIG. 1, for an instrument for therapy of a human eye 1 represents the present state of prior art. It comprises a radiation source 2, which delivers a beam 3 of pulsed laser radiation in the femtosecond range, and a scanning device 4, with which the beam 3 is focussed onto selected positions within the region of the cornea. On the cornea there is a contact glass 5 that has a concave contact surface and suppresses movements of the eye 1 during treatment.

The radiation source 2 is designed, e.g., to deliver laser radiation in the wavelength range around 1040 nm with a pulse width in the region of about 200 fs.

The scanning device 4 has, in the direction of the beam 3 originating from the radiation source 2, an optical assembly 6, behind which in the beam direction, there follows a deflecting device 7. According to given control signals, the deflecting device 7 deflects the beam 3 exiting the optical assembly 6 in a lateral direction, i.e. in X- and Y-direction across the Z-direction of the incident beam 3. In the beam path, the deflecting device 7 is followed by an objective 8, which focuses the beam 3 into the region of the cornea.

The deflecting device 7 is provided with two deflecting mirrors 9 and 9', which can be tilted about axes not shown in FIG. 1. In the simplified representation according to FIG. 1, the mirrors 9 and 9' are aligned in parallel, but actually the tilting axes are orthogonal to one another and to the optical axis of the optical assembly 6, so that tilting the first mirror 9 will deflect the beam 3 in Y-direction, and tilting the second mirror 9' will deflect it in X-direction orthogonal to it. The mirrors 9 and 9' are driven by actuators 10 and 10', respectively, which are connected with a control device via signal paths (marked by arrows). According to the desired focus position in lateral direction, the control device delivers control signals to the actuators 10 and 10', which thereupon cause the mirrors 9 and 9' to tilt.

The optical assembly 6 is provided with a lens 11 of negative refractive power that can be moved relative to the deflecting device 7, and a collecting lens 12. The lens 11 is connected with a straight-line guideway 13 along which it can be shifted with a variable optically effective distance from the deflecting device 7. The shifting of the lens 11 can be actuated, e.g., by a linear drive motor 14, which is also connected to the control device that is not shown. Depending on the desired focus position in Z-direction, the control device generates control signals that go to the linear drive motor 14.

Due to the design of the lens 11 and the collecting lens 12, the optical assembly 6 acts as an expander, which expands the diameter of the beam 3. If, then, a parallel beam 3 having a diameter d1 enters the optical assembly 6, the parallel beam 3 exiting the optical assembly 6 will have a diameter d2>d1.

The objective 8 is shows as a fixed lens 15; it focuses the beam 3 exiting the optical assembly 6 onto a position in the region of the cornea, this position being determined by means of the lens 11 and the deflecting device 7. The position of the focus F in the depth of the region of the cornea is determined by the shifting of the lens 11 along its optical axis. The lateral position of the focus F is determined by the deflecting device 7.

For further details of this, see publication DE 10 2005 013 949 A1.

Departing from the prior art as described above, the problem is solved by the invention in such a way that the objective 8 itself is shiftable along the optical axis or that an objective 8 is provided that consists of several lens groups, with at least one of these lens groups being shiftable along the optical axis. The shifting of the objective 8 or of the lens group of the objective 8 is relative to the eye and relative to the other assemblies of the system, in such a way that this change of distance causes a shift of the focus position from the region of the cornea to the region of the crystalline lens, and vice versa.

Figure 2:
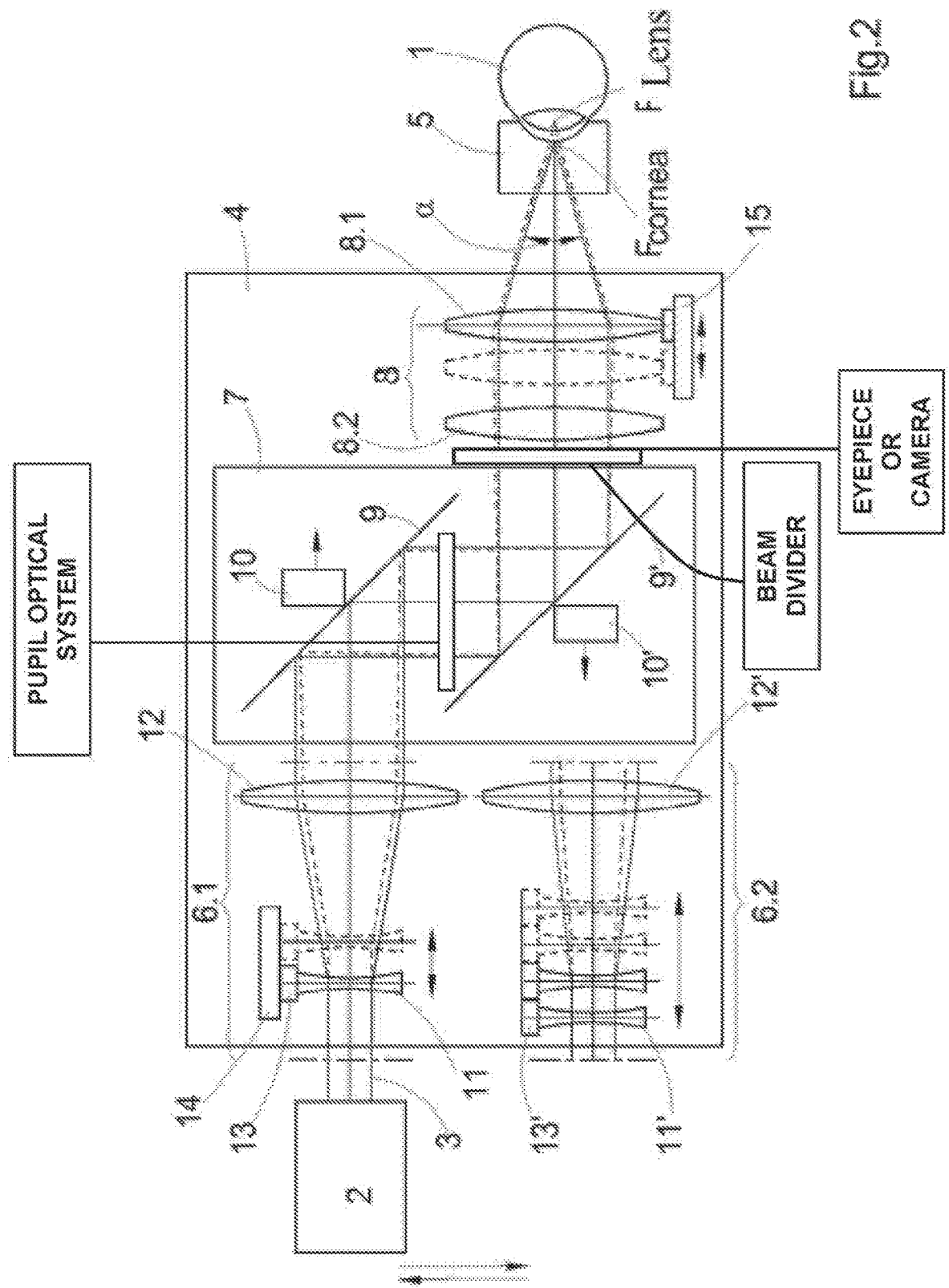
FIG. 2 is a schematic illustration of the invented optical system for a laser therapy instrument in a preferred embodiment.

FIG. 2 illustrates the operating principle of the optical system according to the invention. In this preferred embodiment, the objective 8 consists of two lens groups 8.1 and 8.2, which, for the sake of clarity, are represented symbolically as single lenses. The lens group 8.2 is arranged in a fixed position in the beam path, whereas the lens group 8.1 can be shifted in the direction of the optical axis and, for this purpose, is coupled with a straight-line guideway, which in turn is connected with, e.g., a linear drive motor 15, which initiates the shifting movement and is therefore triggered by a control device (not shown).

The distance by which the lens group 8.1 is shifted, while basically depending on the control signal, is favourably defined by two limit positions, of which a first limit position is marked in FIG. 2 by the lens group 8.1 drawn in solid lines and the second limit position by the same lens group drawn in broken lines.

The fixed shifting distance defined by the limit positions corresponds to the shifting of the focus position from the region of the cornea to the region of the crystalline lens and vice versa, by which it is made fundamentally possible that the laser therapy thus equipped can be used for treatments of both the cornea and the crystalline lens.

As the crystalline lens, as explained before, extends in axial direction over a substantially greater region than the cornea, different focus variation ranges $\Delta z$ are required for the two configurations, and measures must be taken to ensure that, despite the shifting of the focus from the region of the cornea to the region of the crystalline lens and the different focus variation ranges $\Delta z$ required for the two configurations, aberrations are as small as possible and the numerical aperture is a great as possible for the given wavelength of the therapeutic radiation.

According to example embodiments of the invention, this problem is solved by making separate optical assemblies 6.1, 6.2 available as expanders for each configuration and by exchanging these assemblies in the beam path for each other, for example automatically with the shifting of the focus position from the region of the cornea to the region of the crystalline lens and vice versa.

If, for example, the lens group 8.1 is in its first limit position and if at the same time—as shown in FIG. 2—the optical assembly 6.1 is in the beam path between the radiation source 2 and the deflecting device 7, the focus position can be changed—by means of the lens 11 in within a focus variation range $\Delta z1$ in Z-direction and by means of the deflecting device 7 in X- and Y-direction—in such a way that all desired targets within the region of the cornea can be reached with the desired optical precision.

Analogously, this also applies to the second limit position of the lens group 8.1. Simultaneously with the shifting of the lens group 8.1 its second limit position and, thus, the change of system configuration, the optical assembly 6.2 is positioned in the beam path between radiation source 2 and deflecting device 7 in place of the optical assembly 6.1, and thus, it is possible to reach all desired targets within the region of the crystalline lens, and this with the desired optical precision as well. The shifting of the lens 11' in Z-direction now causes the shifting of the focus position within a focus variation range Δz2, which corresponds to the extension of the region of the crystalline lens in the direction of the Z coordinate. The lateral variation of the focus position in X- and Y-direction within this region is accomplished by means of the deflecting device 7.

Since patient's eyes naturally differ in size and particularly in length, in a special embodiment of the invention the position/limit position of the lens group 8.1 for treating the crystalline lens is set as a function of the individual length of the eye, especially of the depth of the anterior chamber.

Both optical assemblies 6.1, 6.2 are so designed that the axially shiftable lenses or lens groups 11 or 11', respectively, in spite of the optical starting parameters brought about by the shifting have one and the same shifting distance, so that one and the same linear drive motor 14 with a specified, fixed shifting distance can be used for both configurations. However, the optical gear ratios of the two assemblies 6.1, 6.2 differ, so that, if the two assemblies 6.1, 6.2 are interchanged, the diameter of the therapeutic laser beam and, consequently, the numerical aperture and/or the eye-side aperture angle of the therapeutic laser radiation will change.

It is essential for the inventive idea that the optical assemblies 6.1, 6.2 consist of several lenses 11, 11', 12, 12' the axial distances between which can be varied. Due to the change of the axial distances, there will be a change of the refractive power situation within the optical assembly concerned, and thus a change of the axial focus position within the focus variation range Δz1 or Δz2, respectively. By contrast, the interchange of the optical assemblies 6.1, 6.2 causes a change of the diameter of the therapeutic laser beam and consequently, a change in the numerical aperture regarding the optical system behind the optical assemblies 6.1, 6.2 in the therapeutic laser beam path, and/or a change in the eye-side aperture angle of the therapeutic laser radiation.

Both optical assemblies 6.1, 6.2 have input and output interfaces in common with the other components of the optical system. The optical parameters at the input interface are always constant, whereas the output parameters vary depending on the optical assembly currently in the beam path and, thus, on the focus position to be set, and are characterized by different divergences and/or beam diameters.

In all embodiment versions of the invention, the changing device can be designed like a magazine, so that each of the two optical assemblies 6.1, 6.2 or also of further optical assemblies is assigned a mounting fixture, with which they, when required, are swivelled into the beam path about an axis of rotation or inserted by means of a straight-line guideway. The basic design of such magazines is known in prior art and needs no detailed description here.

LIST OF REFERENCE NUMBERS

1 eye
2 radiation source
3 radiation beam
4 scanning device
5 contact glass
6 optical assembly
7 deflecting device
8 objective
8.1, 8.2 lens groups
9, 9' mirrors
10, 10' actuators
11, 11' lenses
12, 12' collective lenses
13, 13' straight-line guideway
14 linear drive motor
15 linear drive motor Various embodiments of systems, devices, and methods have been described herein. These embodiments are given only by way of example and are not intended to limit the scope of the claimed inventions. It should be appreciated, moreover, that the various features of the embodiments that have been described may be combined in various ways to produce numerous additional embodiments. Moreover, while various materials, dimensions, shapes, configurations and locations, etc. have been described for use with disclosed embodiments, others besides those disclosed may be utilized without exceeding the scope of the claimed inventions.

Persons of ordinary skill in the relevant arts will recognize that the subject matter hereof may comprise fewer features than illustrated in any individual embodiment described above. The embodiments described herein are not meant to be an exhaustive presentation of the ways in which the various features of the subject matter hereof may be combined. Accordingly, the embodiments are not mutually exclusive combinations of features; rather, the various embodiments can comprise a combination of different individual features selected from different individual embodiments, as understood by persons of ordinary skill in the art. Moreover, elements described with respect to one embodiment can be implemented in other embodiments even when not described in such embodiments unless otherwise noted.

Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims, it is expressly intended that the provisions of 35 U.S.C. § 112(f) are not to be invoked unless the specific terms "means for" or "step for" are recited in a claim.

The invention claimed is:

1. An optical system for a laser therapy instrument, suitable for laser surgery of a cornea and a crystalline lens of a human patient's eye, comprising:
    a femtosecond laser radiation source that emits therapeutic laser radiation,
    an objective from which the therapeutic laser radiation exits and is directed and focussed on to or into the eye,
    at least two optical assemblies that vary the focus of the therapeutic laser radiation, with different focus variation ranges Δz of each of the at least two optical assemblies, and which are insertable into a beam path alternately, thereby limiting an object-side Z scanning range to two separate tissue regions, including a first region encompassing the cornea and a second region encompassing the crystalline lens including the lens capsule.

2. The optical system as claimed in claim 1, in which the objective comprises at least one lens or lens group and is configurable to direct the focus separately to the first region encompassing the cornea in a first configuration, and to the second region encompassing the crystalline lens including the lens capsule in a second configuration, and in which for switching between the first and second configuration of the objective includes at least one of following:
(i) air gaps between single or several lenses of the objective that are changeable,
(ii) lens radii of one or several lenses of the objective that are changeable,
(iii) refractive indices of one or several lenses of the objective that are changeable,
(iv) single lenses or lens groups of the objective that are exchangeable with other single lenses or lens groups, and
(v) further lenses or lens groups that are insertable into the objective.

3. The optical system as claimed in claim 2, further comprising a shifting structure which automatically exchanges the two optical assemblies in the beam path for each other with the shifting of the focus position from the region of the cornea to the region of the crystalline lens and vice versa.

4. The optical system as claimed in claim 2, in which the air gaps between one or several lenses of the objective are changeable and the objective itself or at least one lens or lens group of the objective is shiftable in the direction of the optical axis relative to other lenses or lens groups of the optical system, thereby shifting the focus position between the first region encompassing the cornea and the second region encompassing the crystalline lens and vice versa.

5. The optical system as claimed in claim 4, further comprising a shifting structure which automatically exchanges the two optical assemblies in the beam path for each other with the shifting of the focus position from the region of the cornea to the region of the crystalline lens and vice versa.

6. The optical system as claimed in claim 4, wherein the shifting of the objective or the at least one lens or lens group of the objective in the direction of the optical axis relative to the other lenses or lens groups of the system is dependent on the individual eye length.

7. The optical system as claimed in claim 6, further comprising a shifting structure which automatically exchanges the two optical assemblies in the beam path for each other with the shifting of the focus position from the region of the cornea to the region of the crystalline lens and vice versa.

8. The optical system as claimed in claim 4, wherein the shifting of the objective or the at least one lens or lens group of the objective in the direction of the optical axis relative to the other lenses or lens groups of the system is dependent on a depth of the anterior chamber.

9. A method for laser surgery of the cornea and the crystalline lens of an eye, utilizing a femtosecond laser as a radiation source for therapeutic laser radiation and an objective with lenses or lens groups from which the therapeutic laser radiation exits and is directed and focused on to or into the eye, the method comprising:
configuring the objective in a first configuration wherein a focus is directed to a region of the cornea and limited to a first focus range $\Delta z_1$ encompassing a tissue region of the cornea, and
configuring the objective in a second configuration wherein the focus is directed to a region of the crystalline lens and the lens capsule, and is limited to a second focus range $\Delta z_2$, which is separate from the first focus range $\Delta z_1$ and which encompasses the tissue region of the crystalline lens including the lens capsule in a Z direction.

10. The method as claimed in claim 9, further comprising alternately inserting two optical assemblies that vary the focus of the therapeutic laser radiation, with different focus variation ranges $\Delta z_1$ and $\Delta z_2$ of the individual assemblies, into the beam path when switching between the first and second configuration.

11. The method as claimed in claim 9, further comprising switching the objective between the first and the second configuration by at least one of the following: changing air gaps between single or several lenses of the objective, changing lens radii, changing refractive indices of one or several lenses of the objective, exchanging single lenses or lens groups with other single lenses or lens groups, and by inserting further lenses or lens groups into the objective.

12. The method as claimed in claim 11, further comprising alternately inserting two optical assemblies that vary the focus of the therapeutic laser radiation, with different focus variation ranges $\Delta z_1$ and $\Delta z_2$ of the individual assemblies, into the beam path when switching between the first and second configuration.

13. The method as claimed in claim 11, further comprising shifting the objective or at least one lens or lens group of the objective in the direction of an optical axis and thereby switching the objective between the first and second configuration.

14. The method as claimed in claim 13, further comprising automatically exchanging the two optical assemblies in the beam path for each other when switching between the first and second configuration.

* * * * *

UNITED STATES PATENT AND TRADEMARK OFFICE
CERTIFICATE OF CORRECTION

PATENT NO. : 11,351,061 B2
APPLICATION NO. : 16/684048
DATED : June 7, 2022
INVENTOR(S) : Stobrawa et al.

It is certified that error appears in the above-identified patent and that said Letters Patent is hereby corrected as shown below:

In the Specification

Column 1, Line 7, delete "a" and insert -- is a --, therefor.

Column 1, Line 8, delete "2014." and insert -- 2014, now U.S. Pat. No. 10,478,340, --, therefor.

Column 1, Line 30, delete "then" and insert -- than --, therefor.

Column 3, Line 53, delete "a large" and insert -- as large --, therefor.

Column 5, Line 58, delete "shows" and insert -- shown --, therefor.

Column 6, Line 56, delete "in within" and insert -- within --, therefor.

Column 6, Line 63, delete "its" and insert -- to its --, therefor.

Signed and Sealed this
Eighth Day of August, 2023

Katherine Kelly Vidal
*Director of the United States Patent and Trademark Office*